(12) United States Patent  
Ogawa et al.

(10) Patent No.: US 9,361,818 B2  
(45) Date of Patent: Jun. 7, 2016

(54) OPERATION INPUT DEVICE AND MANIPULATOR SYSTEM

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 735 days.

(21) Appl. No.: 13/669,801

(22) Filed: Nov. 6, 2012

(65) Prior Publication Data  
US 2013/0063580 A1 Mar. 14, 2013

Related U.S. Application Data

(63) Continuation of application No. PCT/JP2011/055050, filed on Mar. 4, 2011.

(30) Foreign Application Priority Data

May 10, 2010 (JP) .................. 2010-108344

(51) Int. Cl.  
A62B 1/04 (2006.01)  
G09G 3/00 (2006.01)  
(Continued)

(52) U.S. Cl.  
CPC *G09G 3/001* (2013.01); *A61B 1/00* (2013.01); *A61B 19/2203* (2013.01);  
(Continued)

(58) Field of Classification Search  
CPC ...... G09G 3/001; A61B 1/00; A61B 19/5244; A61B 19/2203; A61B 2019/2269; A61B 2019/5255; A61B 2019/5214; A61B 2019/5248; A61B 2019/5297; A61B 2019/262; A61B 2019/5257; G06F 3/012; G06F 3/011; B25J 9/1689; B25J 13/02; G05B 2219/45117; G05B 2219/35482  
USPC ........................... 348/43, 65; 345/8; 600/407  
See application file for complete search history.

(56) References Cited

U.S. PATENT DOCUMENTS 7,907,166 B2* 3/2011 Lamprecht et al. ............. 348/43  
2005/0203367 A1* 9/2005 Ahmed et al. ................ 600/407  
2006/0284792 A1* 12/2006 Foxlin ............................. 345/8

FOREIGN PATENT DOCUMENTS

CN 101664339 A 3/2010  
JP 7-110735 A 4/1995  
(Continued)

OTHER PUBLICATIONS

International Search Report dated Jun. 7, 2011 issued in PCT/JP2011/055050.  
English language abstract of Japanese Patent Application Publication No. JP 08-224248 dated Sep. 3, 1996.

*Primary Examiner* — Allen Wong  
(74) *Attorney, Agent, or Firm* — Scully, Scott, Murphy & Presser, P.C.

(57) ABSTRACT

With a simple configuration, a area in which an operating unit can move is prevented from being limited. Provided is an operation input device including a display; an operating unit that operates a display object displayed on the display; a head-mounted unit that is mounted on the head of an operator; relative position sensors that detect a relative position and a relative orientation of one of the head-mounted unit and the operating unit with respect to the other; and a control unit that actuates the display object displayed on the display on the basis of changes in the relative position and the relative orientation detected by the relative position sensors.

10 Claims, 5 Drawing Sheets

(51) Int. Cl.
*A61B 19/00* (2006.01)
*B25J 9/16* (2006.01)
*B25J 13/02* (2006.01)
*G06F 3/01* (2006.01)
*A61B 1/00* (2006.01)

(52) U.S. Cl.
CPC .......... *A61B 19/5244* (2013.01); *B25J 9/1689* (2013.01); *B25J 13/02* (2013.01); *G06F 3/011* (2013.01); *G06F 3/012* (2013.01); *A61B 2019/2269* (2013.01); *A61B 2019/262* (2013.01); *A61B 2019/5214* (2013.01); *A61B 2019/5248* (2013.01); *A61B 2019/5255* (2013.01); *A61B 2019/5257* (2013.01); *A61B 2019/5297* (2013.01); *G05B 2219/35482* (2013.01); *G05B 2219/45117* (2013.01)

(56) References Cited

FOREIGN PATENT DOCUMENTS

| | | |
|---|---|---|
| JP | 7-124165 A | 5/1995 |
| JP | 10-127565 A | 5/1998 |
| JP | 2000-102036 A | 4/2000 |
| JP | 2000-126462 | 5/2000 |
| JP | 2000-279425 A | 10/2000 |
| JP | 2002-269567 A | 9/2002 |
| JP | 3610110 B2 | 10/2004 |
| JP | 2005-500096 | 1/2005 |
| JP | 2008-500624 A | 1/2008 |
| WO | WO 02/100284 A1 | 12/2002 |
| WO | 2005/116809 A2 | 12/2005 |

* cited by examiner

OPERATION INPUT DEVICE AND MANIPULATOR SYSTEM

CROSS REFERENCE TO RELATED APPLICATIONS

This is a continuation of International Application PCT/JP/2011/055050, with an international filing date of Mar. 4, 2011, which is hereby incorporated by reference herein in its entirety. This application is based on Japanese Patent Application No. 2010-108344, the content of which is incorporated herein by reference.

BACKGROUND OF THE INVENTION

1. Field of the Invention

The present invention relates to an operation input device and a manipulator system.

2. Description of Related Art

In the related art, there is a known virtual-experience gaming device in which a sensor for detecting the positions of a display and an operating unit is provided on a ceiling (for example, see Japanese Unexamined Patent Application, Publication No. 2000-126462).

However, with a method in which the positions and orientations of a display and an operating unit are detected by spatial sensors provided on a ceiling, although these devices can be employed in a dedicated room in which there is no obstacle between the ceiling and both the display and the operating unit, it is difficult to employ them in a operating theatre where equipment that acts as an obstacle exists, such as an illumination apparatus, a measuring instrument or the like, and thus, there is a case in that the areas in which the devices can move are limited. With the method in the related art, by obtaining information about the positions and the orientations of the display and the operating unit, each having its own coordinate system, by means of the spatial sensors secured to the ceiling, the relative positional relationship between the display and the operating unit is obtained from the information about the positions and the orientations of the display and the operating unit in the respective spatial-sensor coordinate systems, computations involved in the coordinate transformations are complicated and time consuming.

BRIEF SUMMARY OF THE INVENTION

An object of the present invention is to provide an operation input device and a manipulator system with which, with a simple configuration, an area in which an operating unit can move can be prevented from being limited.

An aspect of the present invention provides an operation input device including a display; an operating unit that operates a display object displayed on the display; a head-mounted unit that is mounted on the head of an operator; a relative position sensor that detects a relative position and a relative orientation of one of the head-mounted unit and the operating unit with respect to the other; and a control unit that actuates the display object displayed on the display on the basis of changes in the relative position and the relative orientation detected by the relative position sensor.

With the above-described aspect, when the operator wearing the head-mounted unit on his or her head operates the operating unit while viewing the display object displayed on the display, the relative position sensor detects a relative position and a relative orientation of one of the head-mounted unit and the operating unit with respect to the other, and the control unit actuates the display object displayed on the display on the basis of changes in the detected relative position and relative orientation. Because the relative position and the relative orientation between the head-mounted unit mounted on the head of the operator and the operating unit operated by the same operator are detected, unlike a conventional method in which a sensor is provided on a ceiling or a wall surface, the area in which the operating unit can move can be prevented from being limited by other obstacles.

In the above-described aspect, the display may be secured to the head-mounted unit so that the display is placed in front of the eyes of the operator when the head-mounted unit is mounted on the head of the operator.

By doing so, the operator wearing the head-mounted unit can perform the operation while viewing the display object displayed on the display placed in front of his or her eyes. With the display mounted on the head of the operator, it is possible to allow the operator to move about.

In the above-described aspect, the relative position sensor may be provided with an indicator provided on one of the head-mounted unit and the operating unit; and an image-acquisition unit that is provided in the other of the head-mounted unit and the operating unit and that captures an image of the indicator.

By doing so, the indicator, provided on one of the head-mounted unit and the operating unit, can be captured by the image-acquisition unit provided in the other, and thereby, it is possible to directly detect the relative position between the head-mounted unit and the operating unit. Because it is possible to obtain information about the relative position/orientation of the operating unit in the sightline coordinate system, for which the viewing field of the operator serves as a reference, by placing the display secured to the head-mounted unit in front of the eyes of the operator, a transformation between the display object displayed on the display and the sightline coordinate system in which it is displayed can be omitted or simplified. Accordingly, the amount of computation can be reduced, making high-speed processing possible, and also enabling intuitive operation.

In the above-described aspect, one image-acquisition unit may be provided.

In this case, the indicators may be provided at at least four locations that are not arranged on the same plane.

By doing so, a change in the relative orientation between the head-mounted unit and the operating unit can be detected by an overall positional change of the indicators at the four locations, and a change in the relative position between the head-mounted unit and the operating unit can be detected by a positional change among the indicators for the indicators at the four locations.

In the above-described aspect, two or more image-acquisition units may be provided.

In this case, the indicators may be provided at at least three locations that are not arranged on the same straight line.

By doing so, a change in the relative orientation between the head-mounted unit and the operating unit can be detected by an overall positional change of the indicators at the three locations, and a change in the relative position between the head-mounted unit and the operating unit can be detected by a positional change among the indicators for the indicators at the three locations.

In the above-described aspect, the relative position sensor may be provided with a sightline detection sensor that can obtain a sightline of the operator. By doing so, it is possible to obtain a more accurate relative position between the sightline of the operator and the operating unit.

In the above-described aspect, at least one of the head-mounted unit and the operating unit may be provided with a spatial sensor that detects information about a displacement in a spatial coordinate system thereof.

By doing so, it is possible to enhance the precision in moving the display object displayed on the display on the basis of the information about displacement of the head-mounted unit or the operating unit in the spatial coordinate system and the relative position and the relative orientation between the head-mounted unit and the operating unit.

It is possible to judge whether or not the relative position or the relative orientation between the head-mounted unit and the operating unit is changed because the head-mounted unit or the operating unit is displaced, and it is possible to more accurately control the actuation of the display object by means of the control unit.

In the above-described aspect, the display may be provided with a display indicator that is fixed in the spatial coordinate system thereof and an image of which is captured by the image-acquisition unit provided in the other of the head-mounted unit and the operating unit.

By doing so, the display indicators, provided on the display fixed in the spatial coordinate system, can be captured by the image-acquisition unit, and thus, the angle and position of the display with respect to the image-acquisition unit can be detected. Accordingly, even if the operator moves relative to the display, the angle and direction of the display object can be adjusted, and it is possible to always maintain the coordinates of the display object constant with respect to the sight-line coordinate system of the operator.

An aspect of the present invention provides a manipulator system including one of the above-described operation input devices; a manipulator that is the display object; and an observation device that obtains a video image of the display object displayed on the display.

By doing so, the video image of the manipulator, which is the display object, obtained by the observation device is displayed on the display, and the control unit actuates the manipulator depending on changes in the relative position and the relative orientation between the operating unit, provided in the operation input device, and the head-mounted unit. Accordingly, it is possible to perform treatment by using the manipulator while preventing the area in which the operating unit can move from being limited by other obstacles.

The present invention affords an advantage in that, with a simple configuration, an area in which an operating unit can move can be prevented from being limited and to reduce calculation costs due to laborious coordinate transformations.

DETAILED DESCRIPTION OF THE INVENTION

An operation input device and a manipulator system according to an embodiment of the present invention will be described below with reference to the drawings.

Figure 1:
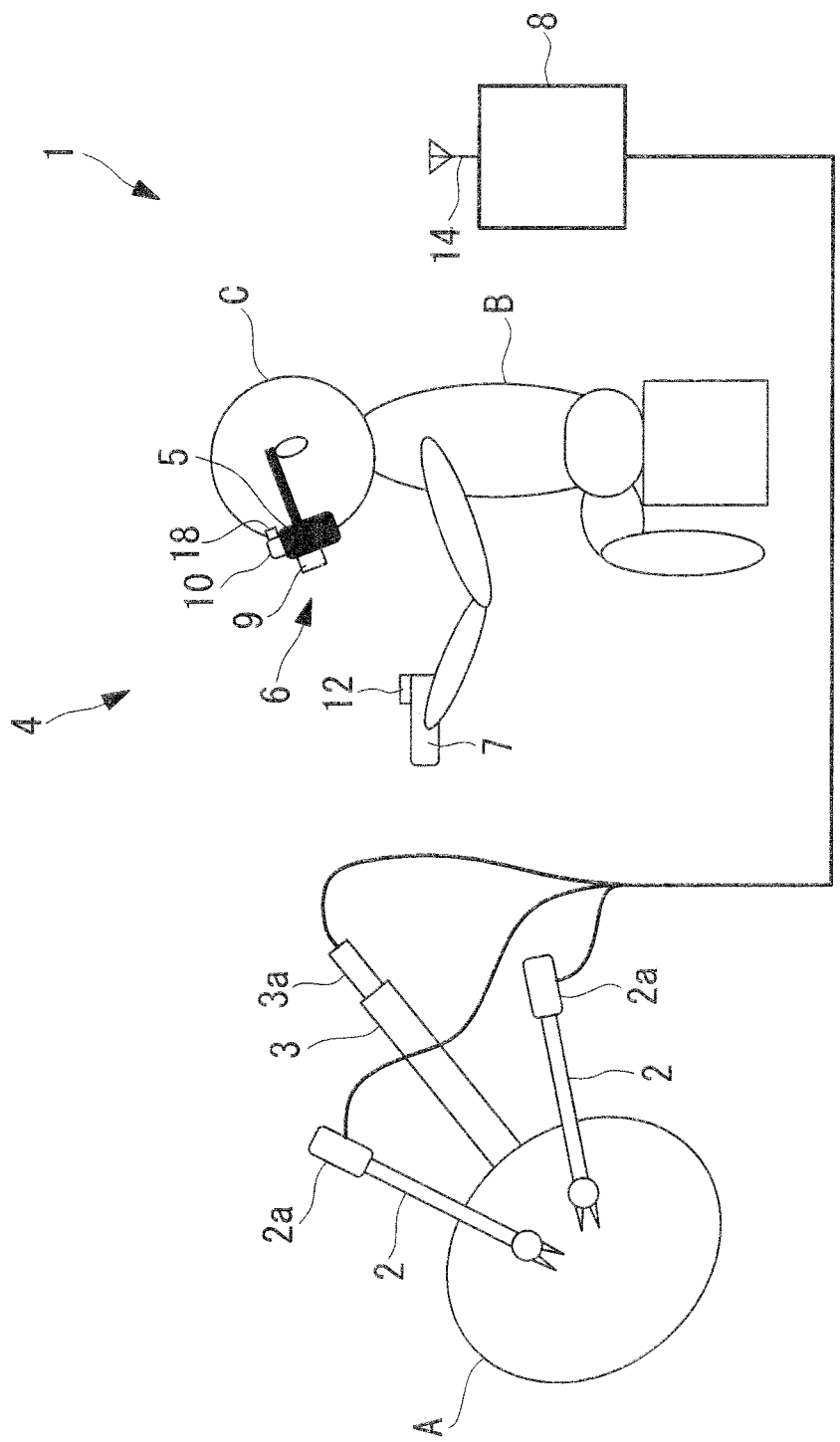
FIG. 1 is an overall configuration diagram showing a manipulator system according to an embodiment of the present invention.

As shown in FIG. 1, a manipulator system 1 according to this embodiment is provided with a manipulator 2 that is inserted into the body of a patient A, an endoscope (observation device) 3 that captures a video image of the manipulator 2, and an operation input device 4 according to this embodiment.

In the example shown in FIG. 1, two manipulators 2 are provided, for each of which the orientation, position, and actuation status thereof can be individually changed by means of a motor 2a. Also, the orientation, position, and actuation status of the endoscope 3 can be changed by means of a motor 3a.

The operation input device 4 according to this embodiment is provided with a display unit (display) 5 that displays a video image of the manipulators 2 obtained by the endoscope 3 inside the body of the patient A, and is provided with a head-mounted display (head-mounted unit: hereinafter, referred to as HMD (Head Mounted Display)) 6 that is mounted on a head C of an operator B, an operating unit 7 that is operated by the operator B, and a control unit 8 that actuates the manipulators 2 depending on the operation of the operating unit 7.

The HMD 6 is configured so that the display unit 5 is placed in front of the eyes of the operator B in a state in which it is mounted on the head C of the operator B. The HMD 6 is provided with an image-acquisition unit (relative position sensor) 9, such as a CCD, having a viewing field that makes it possible to capture an image in front of the head C of the operator B, in the state in which the HMD 6 is mounted on the head C of the operator B, and an acceleration sensor (spatial sensor) 10 that detects acceleration in the spatial coordinate system of the HMD 6.

Figure 2:
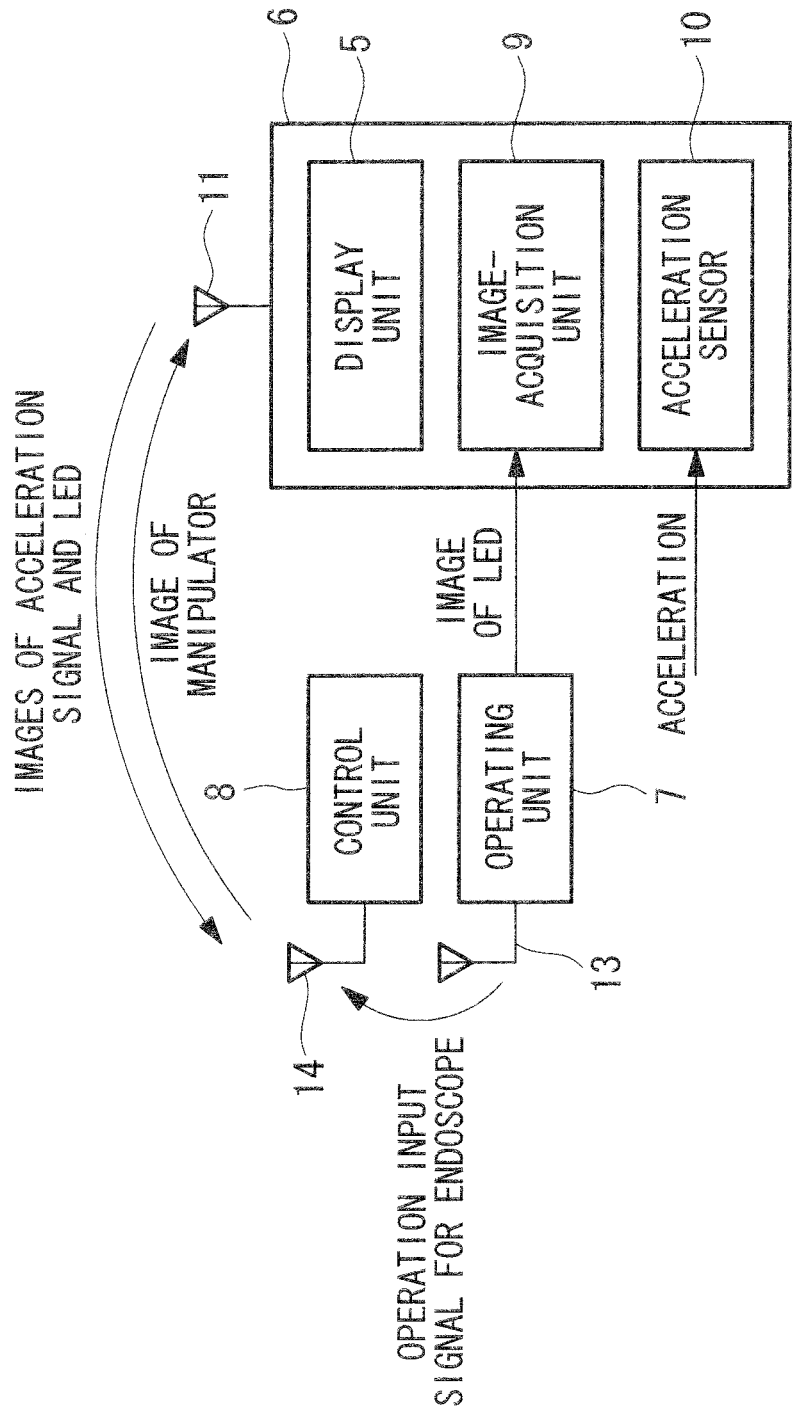
FIG. 2 is a block diagram showing an operation input device according to this embodiment provided in the manipulator system in FIG. 1.

As shown in FIG. 2, the HMD 6 is provided with a transmitting unit 11 that wirelessly transmits an image signal captured by the image-acquisition unit 9 and an acceleration signal in the spatial coordinate system of the HMD 6, detected by the acceleration sensor 10.

The operating unit 7 is configured so that the manipulators 2 and the endoscope 3 can be operated by the operator B holding and operating it in his or her hands. Four LEDs (indicators: relative position sensors) 12 that emit light, arranged at positions that are not arranged on the same plane, are secured to the operating unit 7. The operating unit 7 is provided with a transmitting unit 13 that wirelessly transmits operation input signals for the manipulators 2 and the endoscope 3.

The control unit 8 is provided with a transmitting/receiving unit 14 that, upon receiving an input image signal obtained by the endoscope 3, processes the image signal and transmits it to the HMD 6 so that the captured image is displayed on the display unit 5 provided in the HMD 6.

The control unit 8 receives, by means of the receiving unit 14, the image signal and the acceleration signal wirelessly transmitted from the HMD 6, as well as the operation input signals wirelessly transmitted from the operating unit 7; generates control signals for moving the manipulators 2; and activates the motors 2a of the manipulators 2 on the basis of the generated control signals, thereby moving the manipulators 2 or changing the actuation status thereof. It is also possible to activate the motor 3a of the endoscope 3 on the basis of these control signals to move the endoscope 3 or to change the actuation status thereof.

Specifically, the control unit 8 processes the image obtained by the image-acquisition unit 9 provided in the HMD 6 and calculates a relative position and a relative orientation of the operating unit 7 with respect to the HMD 6 in accordance with the positions and spacing of the LEDs 12 on the operating unit 7 captured by the image-acquisition unit 9. The control unit 8 calculates a position and an orientation of the HMD 6 in the spatial coordinate system on the basis of the acceleration signal output from the acceleration sensor 10 provided in the HMD 6.

When the relative position and the relative orientation of the operating unit 7 with respect to the HMD 6 change, the control unit 8 judges whether the changes are due to a displacement of the HMD 6 or a displacement of the operating unit 7 by means of the acceleration signal from the acceleration sensor 10; generates a control signal for moving the endoscope 3 in response to the portion due to the displacement of the HMD 6; and generates control signals for the manipulators in response to the portion due to the displacement of the operating unit 7.

In other words, the positions and spacing of the LEDs 12 obtained by the image-acquisition unit 9 can be changed when the HMD 6 is fixed and the operating unit 7 is displaced, as well as when the operating unit 7 is fixed and the HMD 6 is displaced. However, with regard to the displacement level of the HMD 6 detected by the acceleration sensor 10, because it is caused by the operator B moving his or her head C, the endoscope 3 can be controlled by the control signal based on this displacement level of the HMD 6, and the manipulators 2 can be actuated by using the portion due to the displacement of the operating unit 7 excluding the displacement level of the HMD 6 as the control signal therefor. With regard to the movement of the endoscope 3, by providing a filter or a threshold for the displacement of the HMD 6, control modes therefor can be selected, such as stop, move, or the like.

In this way, with the manipulator system 1 and the operation input device 4 according to this embodiment, because the image-acquisition unit 9 that detects the relative position and the relative orientation of the operating unit 7, which is held by the operator B in his or her hands, with respect to the HMD 6 is disposed on the HMD 6 mounted on the head C of the operator B, the space between the two is not blocked by an obstacle, such as an illumination apparatus, a measuring instrument, or the like, even if the operator B moves about, and thus, an area in which the operating unit 7 moves can be prevented from being limited. In other words, the operator B can operate the manipulators 2 by freely positioning and freely orienting himself/herself.

Relative three-dimensional information about the operating unit 7 with respect to a sightline coordinate system of the operator B, which is fixed to the HMD 6, can be directly obtained by the image-acquisition unit 9 provided in the HMD 6. As a result, an advantage is afforded in that coordinate transformations by the control unit 8 can be reduced, which makes it possible to perform computations at high speed.

By mounting a sightline detection sensor 18 that can obtain the sightline of the operator on the HMD 6, it is possible to obtain a more accurate relative position between the sightline of the operator and the operating unit.

Although a sensor having the image-acquisition unit 9 provided in the HMD 6 and the four LEDs 12 provided in the operating unit 7 has been described as the example of an relative position sensor in this embodiment, alternatively, the image-acquisition unit 9 may be provided in the operating unit 7 and the LEDs 12 may be provided in the HMD6.

By providing two image-acquisition units 9, the relative position may be obtained, assuming that three LEDs are attached to the operating unit 7 or the HMD 6. In this case, the LEDs, that is, indicators, are arranged and secured at positions that are not arranged on the same straight line. In addition, it suffices to have the indicators at at least three locations. Furthermore, two or more image-acquisition units may be provided.

Although it is assumed that the spatial sensor formed of the acceleration sensor 10 is provided in the HMD 6, alternatively, it may be provided in the operating unit 7.

With regard to the acceleration sensor 10, it may be provided both in the HMD 6 and the operating unit 7. By doing so, operation is possible even in the case in which an operational failure occurs in the image-acquisition unit 9. On the other hand, by correcting the relative position and the relative orientation by using detection values from one of the acceleration sensors 10, an advantage is afforded in that detection precision can be enhanced.

In the case in which both the HMD 6 and the operating unit 7 are provided with the acceleration sensors 10, the relative position may be detected by the image-acquisition unit 9 and at least one indicator, and the relative orientation may be obtained by means of the acceleration sensor 10.

Figure 3:
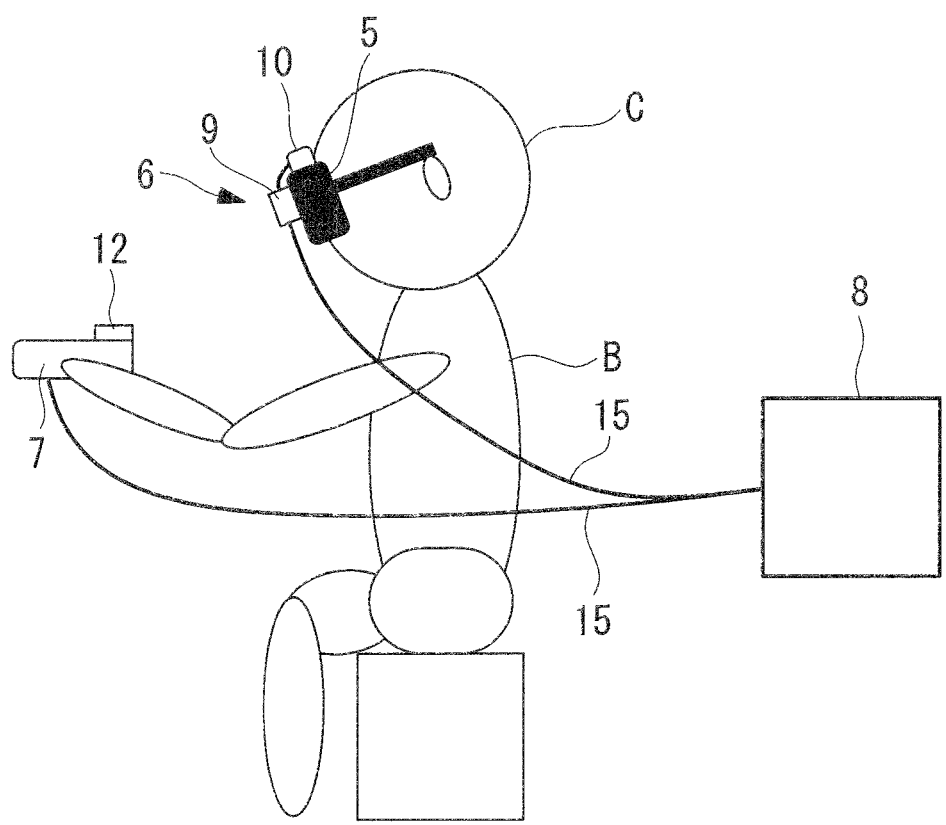
FIG. 3 is an overall configuration diagram showing a modification of the operation input device in FIG. 2.
Figure 4:
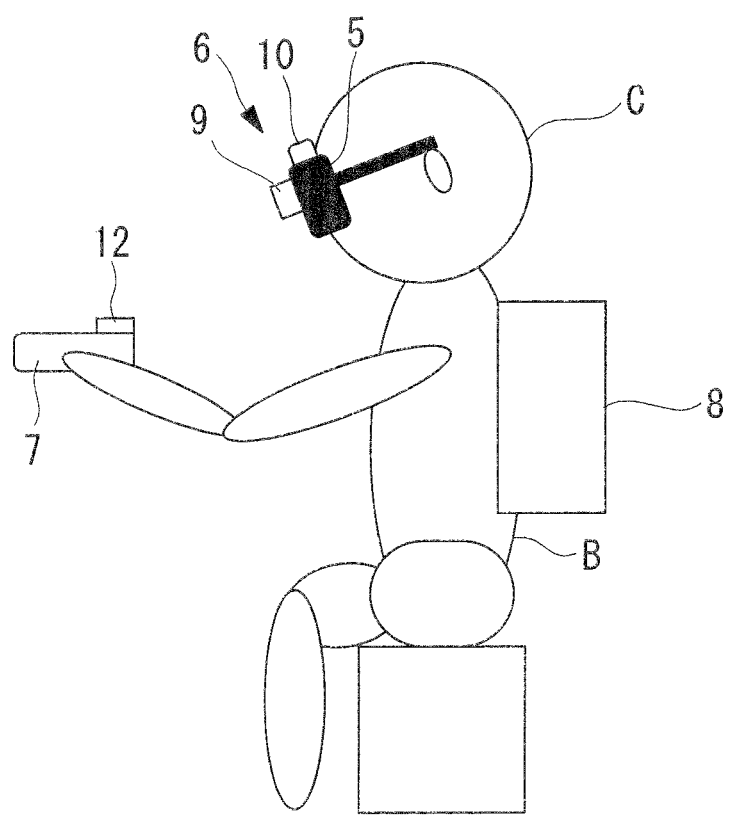
FIG. 4 is an overall configuration diagram showing another modification of the operation input device in FIG. 2.

Although it is assumed that the signals from the operating unit 7 and the HMD 6 are transmitted to the control unit 8 by means of wireless transmission, alternatively, as shown in FIG. 3, wired transmission may be used by connecting the HMD 6 and the operating unit 7 to the control unit 8 by means of wires 15. The operator B may be allowed to move more freely by mounting the control unit 8 on the operator B, as shown in FIG. 4.

Figure 5:
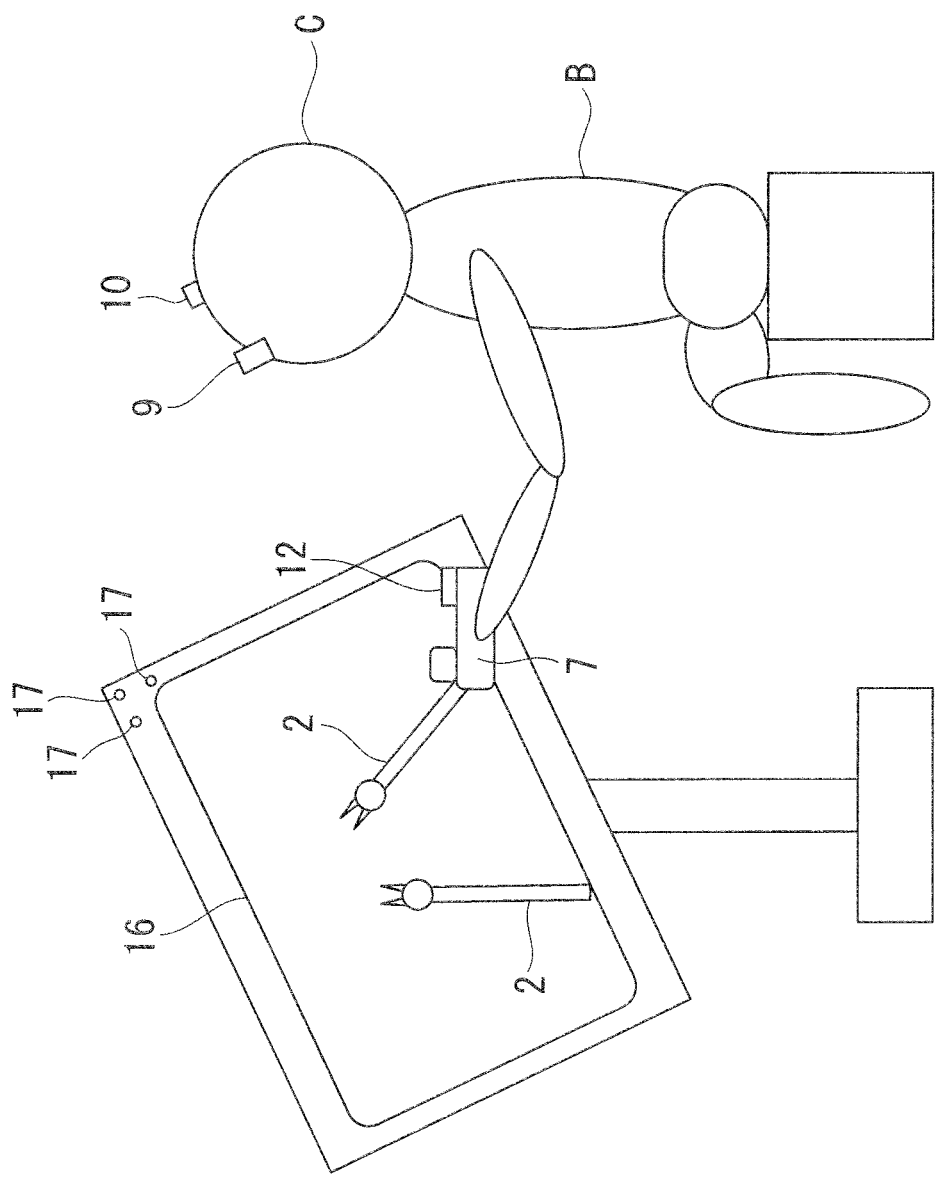
FIG. 5 is an overall configuration diagram showing another modification of the operation input device in FIG. 2.

Although the HMD 6 having the display unit 5 which is placed in front of the eyes of the operator B has been described as an example of a head-mounted unit in this embodiment, alternatively, as shown in FIG. 5, only the image-acquisition unit 9 and the acceleration sensor 10 may be secured to the head C of the operator B and, as for the display unit 5, a separately placed display 16 fixed in the spatial coordinate system may be employed. In this case, because the relative positional relationship and the relative angle between the operator B and the display 16 change due to the movement of the operator B, if the display is not changed, the operator B must understand the movement of the manipulators 2 displayed on the display 16 by mentally performing a transformation.

Therefore, by changing the display by providing the display 16 with LEDs (display indicators) 17 that are similar to the ones described above and by detecting the relative positional relationship between the head C of the operator B and the display 16 by means of the image-acquisition unit 9 and the acceleration sensor 10 provided on the head C of the operator B, it becomes possible to display the movement of the manipulators 2 always in the same state with respect to the operator B without requiring the mental transformation.

Although the four LEDs 12 that are not arranged on the same plane have been described as examples of indicators in this embodiment, alternatively, fluorescent markers or other arbitrary indicators may be employed Five or more indicators may be provided.

Although the acceleration sensor 10 has been described as an example of a spatial sensor in this embodiment, alternatively, a gyro sensor or a velocity sensor may be employed. In addition, a combination thereof may be employed.

The invention claimed is:
1. An operation input device comprising:
a display;
an operating unit that operates a display object displayed on the display;
a head-mounted unit that is mounted on the head of an operator;

a relative position sensor that detects a relative position and a relative orientation of one of the head-mounted unit and the operating unit with respect to the other; and a control unit that actuates the display object displayed on the display on the basis of changes in the relative position and the relative orientation detected by the relative position sensor, wherein the relative position sensor comprises:
an indicator provided on one of the head-mounted unit and the operating unit; and
an image-acquisition unit that is provided in the other of the head-mounted unit and the operating unit and that captures an image of the indicator.

2. An operation input device according to claim 1, wherein the display is secured to the head-mounted unit so that the display is placed in front of the eyes of the operator when the head-mounted unit is mounted on the head of the operator.

3. An operation input device according to claim 1, wherein one image-acquisition unit is provided.

4. An operation input device according to claim 3, wherein the indicators are provided at at least four locations that are not arranged on the same plane.

5. An operation input device according to claim 1, wherein two or more image-acquisition units are provided.

6. An operation input device according to claim 5, wherein the indicators are provided at at least three locations that are not arranged on the same straight line.

7. An operation input device according to claim 1, wherein the relative position sensor is provided with a sightline detection sensor that can obtain a sightline of the operator.

8. An operation input device according to claim 1, wherein at least one of the head-mounted unit and the operating unit is provided with a spatial sensor that detects information about a displacement in a spatial coordinate system thereof.

9. An operation input device according to claim 1, wherein the display is provided with a display indicator that is fixed in the spatial coordinate system thereof and an image of which is captured by the image-acquisition unit provided in the other of the head-mounted unit and the operating unit.

10. A manipulator system comprising:
an operation input device according to claim 1;
a manipulator that is the display object; and
an observation device that obtains a video image of the display object displayed on the display.

* * * * *